(12) United States Patent
Keranen et al.

(10) Patent No.: US 10,607,734 B2
(45) Date of Patent: Mar. 31, 2020

(54) SYSTEMS AND METHODS FOR GENERATING WORKFLOW OUTPUTS

(71) Applicants: VARIAN MEDICAL SYSTEMS, Inc., Palo Alto, CA (US); VARIAN MEDICAL SYSTEMS INTERNATIONAL AG, Cham (CH)

(72) Inventors: Wayne Keranen, Fenton, MI (US); Jukka Suominen, Cham (CH); Aleksi Nurmi, Cham (CH); Janne Sauvala, Espoo (FI); Seppo Tuomaala, New York, NY (US); Martin Sabel, Hagendorn (CH); Joakim Pyyry, Helsinki (FI); Ramin Baghaie, Cham (CH)

(73) Assignees: VARIAN MEDICAL SYSTEMS, INC., Palo Alto, CA (US); VARIAN MEDICAL SYSTEMS, INTERNATIONAL AG, Cham (CH)

( * ) Notice: Subject to any disclaimer, the term of this patent is extended or adjusted under 35 U.S.C. 154(b) by 453 days.

(21) Appl. No.: 14/874,340

(22) Filed: Oct. 2, 2015

(65) Prior Publication Data
US 2017/0097757 A1   Apr. 6, 2017

(51) Int. Cl.
*G06F 19/00* (2018.01)
*G06T 11/20* (2006.01)
*G16H 40/20* (2018.01)

(52) U.S. Cl.
CPC ............. *G16H 40/20* (2018.01); *G06F 19/00* (2013.01)

(58) Field of Classification Search
CPC .. G06F 19/321; G06F 19/3418; G06F 19/325; G06F 3/04845; G06F 8/34; G06F 3/067; G06F 9/451; G06Q 50/24; G06Q 10/06; G06Q 10/0633; G06Q 10/10; H04L 67/025; G06N 20/00; G06N 3/02
See application file for complete search history.

(56) References Cited

U.S. PATENT DOCUMENTS

| | | | |
|---|---|---|---|
| 6,624,908 B1 * | 9/2003 | Petchenkine | G06Q 10/06 358/1.15 |
| 2009/0099871 A1 * | 4/2009 | Gadodia | G06Q 10/06 705/3 |
| 2016/0154938 A1 * | 6/2016 | Becker | G06F 19/327 702/189 |

* cited by examiner

Primary Examiner — Maroun P Kanaan
(74) Attorney, Agent, or Firm — Duane Morris LLP; Manita Rawat

(57) ABSTRACT

A system generally includes at least one computing device having a user interface and a display interface. The computing device is configured to generate at least one desktop that can be viewed by a user via the display interface and to access a plurality of functionality modules that are each configured to receive at least one radiotherapy parameter. The computing device is configured to enable the user, via the user interface, to place the functionality modules onto the desktop. The computing device is configured to enable the user, via the user interface, to connect one of the placed functionality modules to at least another one to commence the generation of at least one workflow output. The computing device is also configured to enable the user, via the user interface, to connect a plurality of input components to the placed functionality modules to finalize the generation of the workflow output.

20 Claims, 9 Drawing Sheets

SYSTEMS AND METHODS FOR GENERATING WORKFLOW OUTPUTS

BACKGROUND

In systems, such as radiation therapy systems, ionizing radiation techniques are used to treat various tissues, such as tumors. At least some known ionizing radiation techniques that are used in radiation therapy systems include electron beams, x-rays, and proton beams. These techniques enable a radiologist to treat patients from multiple angles, while also varying the shape and dose of the radiation beam. This approach also enables the delivery of radiation to a target within a treatment volume while avoiding excess irradiation of adjacent healthy tissue. In order to deliver radiation appropriately, treatment plans, including workflow outputs and/or reports, are used. At least some known treatment plans consider various parameters, such as dosage of radiation, treatment volume, and maximum dosage that can be safely absorbed by tissue.

In generating such treatment plans, including workflow outputs, and/or reports, computing devices and/or computing systems can be used. However, software and/or computer programs that are directed towards generating such treatment plans can be tedious, as they are not user-friendly. For example, at least some known software tools and/or computer programs can require the user to be a programmer to generate workflow outputs and/or reports. Moreover, a user may be unable to directly modify any computer generated code to adjust the plan and the user may be unable to save a unique report that is designed specifically for a patient that can be viewed by other users.

BRIEF DESCRIPTION

The embodiments described herein facilitate a user-friendly platform such that users who are not programmers can generate workflow outputs and/or reports for the radiation therapy treatment of a patient, wherein the user is enabled to connect and/or modify various aspects of the workflow outputs and generate reports that can be accessible to various users. For example, in some embodiments, a system is provided that includes at least one computing device having a user interface and a display interface. The computing device is configured to generate at least one desktop that can be viewed by a user via the display interface and to access a plurality of functionality modules, such as action packs, that are each configured to receive at least one radiotherapy parameter. The computing device is further configured to enable the user, via the user interface, to place the functionality modules onto the desktop. The computing device is configured to enable the user, via the user interface, to connect one of the placed functionality modules to at least another one of the placed functionality modules to commence the generation of at least one workflow output. The computing device is also configured to enable the user, via the user interface, to connect a plurality of input components to the placed functionality modules to finalize the generation of the workflow output.

In other embodiments, a method for generating at least one workflow output using a computing device that includes a user interface and a display interface is provided, wherein the method includes generating at least one desktop, via the computing device, that can be viewed by a user via the display interface. A plurality of functionality modules, such as action packs, are accessed such that each are configured to receive at least one radiotherapy parameter. The user is enabled, via the user interface, to place the functionality modules onto the desktop. The method also includes enabling the user, via the user interface, to connect one of the placed functionality modules to at least another one of the placed functionality modules to commence the generation of at least one workflow output. The user is also enabled to connect a plurality of input components to the placed functionality modules, via the user interface, to finalize the generation of the workflow output.

In some embodiments, at least one computer-readable storage medium having computer-executable instructions embodied thereon is provided, wherein, when executed by at least one processor, the computer-executable instructions cause the processor to generate at least one desktop that can be viewed by a user via a display interface and to access a plurality of functionality modules, such as action packs, that are each configured to receive at least one radiotherapy parameter. The computer-executable instructions also cause the processor to place the functionality modules onto the desktop, based on at least one instruction received from the user via a user interface. In addition, the computer-executable instructions cause the processor to connect one of the placed functionality modules to at least another one of the placed functionality modules, based on at least one instruction received from the user via the user interface, to commence the generation of at least one workflow output. The computer-executable instructions further cause the processor to connect a plurality of input components to the placed functionality modules, based on at least one instruction received from the user via the user interface, to finalize the generation of the workflow output.

DETAILED DESCRIPTION

Figure 1:
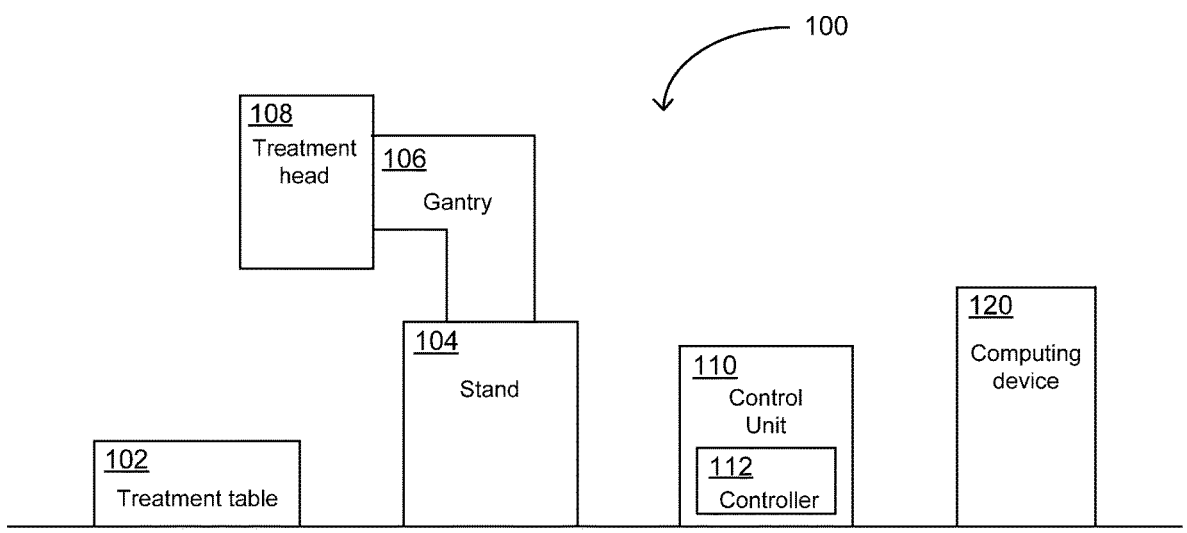
FIG. 1 is a block diagram of an exemplary system.

The following disclosure provides many different embodiments, or examples, for implementing different features of the subject matter. Specific examples of components and arrangements are described below to simplify the present disclosure. These are, of course, merely examples and are not intended to be limiting. For example, the formation of a first feature over or on a second feature in the description that follows may include embodiments in which the first and second features are formed in direct contact, and may also include embodiments in which additional features may be formed between the first and second features, such that the first and second features may not be in direct contact. In addition, the present disclosure may repeat reference numerals and/or letters in the various examples. This repetition is for the purpose of simplicity and clarity and does not in itself dictate a relationship between the various embodiments and/or configurations discussed.

In describing the various embodiments herein, "radiation" refers to any particles (e.g., photons, electrons, protons etc.) used to treat tissue, e.g., tumors. Examples of radiation include high energy x-rays, gamma rays, electron beams, and proton beams. The different particles can correspond to different types of radiation treatments. The "treatment volume" refers to the entire volume that will be subjected to radiation, and is sometimes referred to as the "irradiated volume." The "target structure", "target volume", and "planning target volume" ("PTV") refer to tissue intended to receive a therapeutic prescribed dose. A "treatment plan" can include workflow outputs and/or reports with a dose distribution and/or machine parameters for achieving the dose distribution for a given patient, and information about the given patient. A dose distribution provides information about the variation in the dose of radiation with position. A "dose distribution" can take many forms, e.g., a dose volume histogram ("DVH") or a dose matrix.

As described above, in generating various types of treatment plans, including workflow outputs and/or reports, computing devices and/or computing systems can be used. However, at least some known software tools and/or computer programs can require the user to be a programmer to generate workflow outputs and/or reports. The embodiments of the system(s) and method(s) described herein facilitate a user-friendly platform such that users who are not programmers can readily generate workflow outputs and/or reports for the radiation therapy treatment of a patient, wherein the user is enabled to chain and/or modify various aspects of the workflow outputs and generate reports that can be accessible to various users.

FIG. 1 illustrates a block diagram of an exemplary system 100, such as a radiation therapy system, that is configured to treat affected tissue, such as cancer tissue, on a patient. In some embodiments, system 100 is configured to generate an electron (particle) beam or an x-ray (photon) beam for use in the radiation therapy or radiotherapy treatment of patients on a treatment table 102. In some embodiments, system 100 is configured to generate heavy ion particles, such as protons. System 100 includes a stand 104, which supports a rotatable gantry 106 with a treatment head 108.

A control unit 110 is positioned next to stand 104, wherein control unit 110 includes a controller 112 that is configured for controlling the different modes of operation of an accelerator (not shown). For example, controller 112 can be configured to facilitate operative features of various components of the accelerator, via features that include, without limitation, receiving inputs and/or transmitting outputs. In some embodiments, controller 112 can be a real-time controller and can include any suitable processor-based or microprocessor-based system, such as a computer system, that includes microcontrollers, reduced instruction set computer ("RISC"), an embedded microprocessor, application-specific integrated circuits ("ASICs"), logic circuits, and/or any other circuit or processor that is capable of executing the functions described herein. In some embodiments, controller 112 can be a microprocessor that includes read-only memory ("ROM") and/or random access memory ("RAM"), such as, for example, a 32 bit microcomputer with 2 Mbit ROM and 64 Kbit RAM. As used herein, the term "real-time" refers to outcomes occurring within a short period of time after a change in the inputs affect the outcome, with the time period being a design parameter that can be selected based on the importance of the outcome and/or the capability of the system processing the inputs to generate the outcome.

In some embodiments, system 100 also includes a user computing device 120 that can be coupled to controller 112. Computing device 120 can be a desktop computer, laptop, mobile device, tablet, thin client, or other suitable device that enables system 100 to function as described herein.

Figure 2:
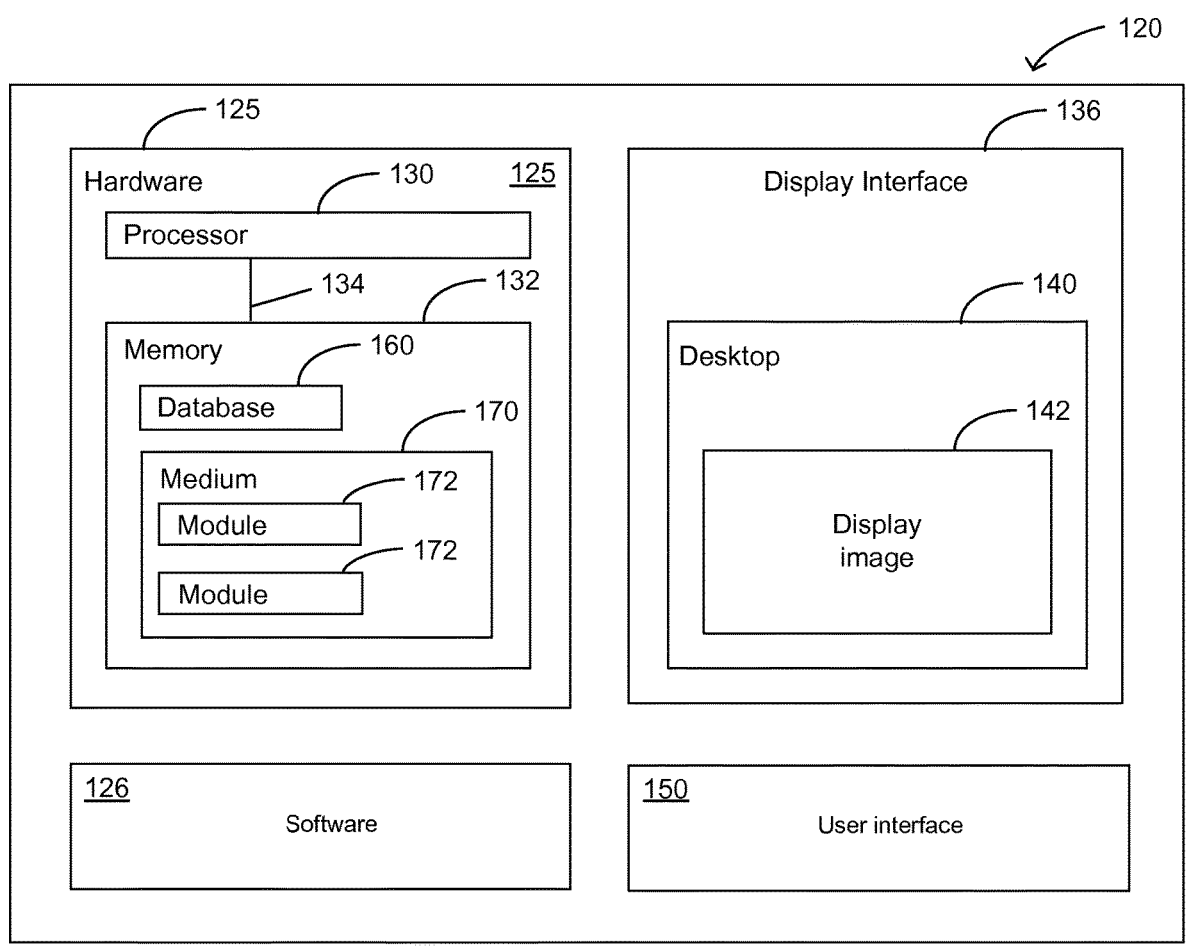
FIG. 2 is a block diagram of exemplary computing device that can be used with the system shown in FIG. 1.

FIG. 2 illustrates a block diagram of computing device 120. In some embodiments, computing device 120 includes a hardware unit 125 and software 126. Software 126 can run on hardware unit 125 such that various applications or programs can be executed on hardware unit 125 by way of software 126. In some embodiments, the functions of software 126 can be implemented directly in hardware unit 125, e.g., as a system-on-a-chip, firmware, field-programmable gate array ("FPGA"), etc. In some embodiments, hardware unit 125 includes one or more processors, such as processor 130. In some embodiments, processor 130 is an execution unit, or "core," on a microprocessor chip. In some embodiments, processor 130 may include a processing unit, such as, without limitation, an integrated circuit ("IC"), an ASIC, a microcomputer, a programmable logic controller ("PLC"), and/or any other programmable circuit. Alternatively, processor 130 may include multiple processing units (e.g., in a multi-core configuration). The above examples are exemplary only, and, thus, are not intended to limit in any way the definition and/or meaning of the term "processor."

Hardware unit 125 also includes a system memory 132 that is coupled to processor 130 via a system bus 134. Memory 132 can be a general volatile RAM. For example, hardware unit 125 can include a 32 bit microcomputer with 2 Mbit ROM and 64 Kbit RAM, and/or a few GB of RAM. Memory 132 can also be a ROM, a network interface (NIC), and/or other device(s).

In some embodiments, computing device 120 can also include at least one media output component or display interface 136 for use in presenting information to a user. Display interface 136 can be any component capable of conveying information to a user and may include, without limitation, a display device (not shown) (e.g., a liquid crystal display ("LCD"), an organic light emitting diode ("OLED") display, or an audio output device (e.g., a speaker or headphones)). In some embodiments, computing device 120 can output at least one desktop, such as desktop 140. Desktop 140 can be an interactive user environment provided by an operating system and/or applications running within computing device 120, and can include at least one screen or display image, such as display image 142. Desktop 140 can also accept input from a user in the form of device inputs, such as keyboard and mouse inputs. In some embodiments, desktop 140 can also accept simulated inputs, such as simulated keyboard and mouse inputs. In addition to user input and/or output, desktop 140 can send and receive device data, such as input and/or output for a FLASH memory device local to the user, or to a local printer.

In some embodiments, display image 142 can be presented to a user on computer displays of a remote terminal (not shown). For example, computing device 120 can be connected to one or more remote terminals (not shown) or servers (not shown) via a network (not shown), wherein the network can be the Internet, a local area network ("LAN"), a wide area network ("WAN"), a personal area network ("PAN"), or any combination thereof, and the network can transmit information between computing device 120 and the remote terminals or the servers, such that remote end users can access the information from computing device 120.

In some embodiments, computing device 120 includes an input or a user interface 150 for receiving input from a user. User interface 150 may include, for example, a keyboard, a pointing device, a mouse, a stylus, a touch sensitive panel (e.g., a touch pad or a touch screen), a gyroscope, an accelerometer, a position detector, and/or an audio input device. A single component, such as a touch screen, may function as both an output device of the media output component and the input interface. In some embodiments, mobile devices, such as tablets, can be used.

Computing device 120, in some embodiments, can include a database 160 within memory 132, such that various information can be stored within database 160. Alternatively, in some embodiments, database 160 can be included within a remote server (not shown) with file sharing capabilities, such that database 160 can be accessed by computing device 120 and/or remote end users. In some embodiments, a plurality of computer-executable instructions can be stored in memory 132, such as one or more computer-readable storage mediums 170 (only one being shown in FIG. 2). Computer storage medium 170 includes non-transitory media and may include volatile and nonvolatile, removable and non-removable mediums implemented in any method or technology for storage of information such as computer-readable instructions, data structures, program modules or other data. The instructions may be executed by processor 130 to perform the functions described in more detail below. For example, in some embodiments, medium 170 can store one or more functionality modules or action packs 172 (only two being shown in FIG. 3) that have been generated and/or implemented by software 126, wherein each functionality module 172 is associated with a different performance task and each module 172 can be configured to receive at least one radiation therapy or radiotherapy parameter or object, such patient information, course information, image(s), plan(s), dose, DVH, etc.

During operation of system 100 (shown in FIG. 1) and computing device 120, a user, who may not be a programmer, is enabled to generate workflow outputs and/or reports for the radiation therapy treatment of a patient by system 100. As explained in more detail below with respect to FIGS. 3 and 4A-4F, a user is enabled to chain or connect various aspects of workflow outputs and generate reports that can be accessible to various users. For example, in some embodiments, generated functionality modules 172 can be viewed by the user on desktop 142, via display interface 136, and the user can drag and connect modules 172 within desktop 142 to generate at least one workflow output and/or report.

Figure 3:
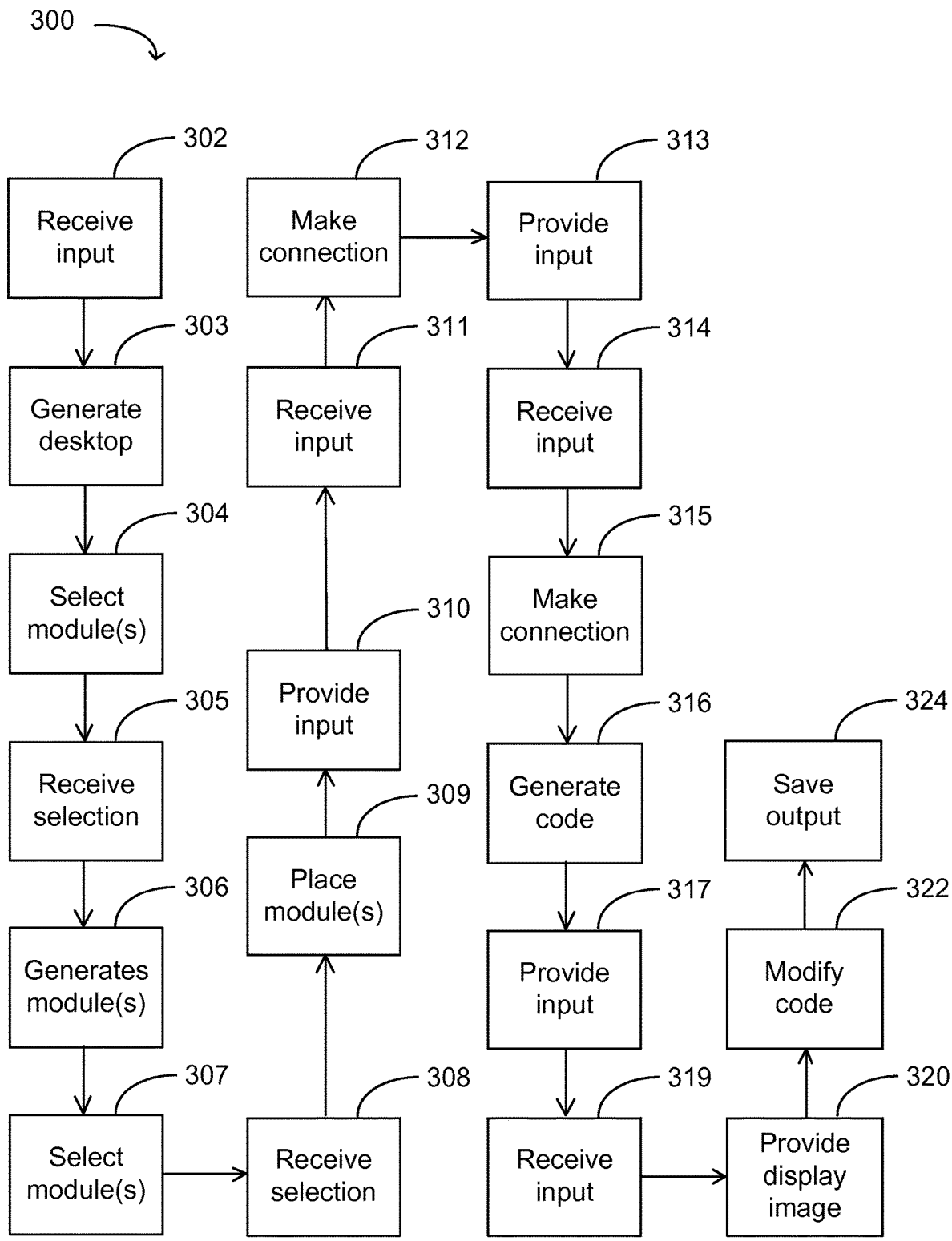
FIG. 3 is a flow diagram of an exemplary method for generating at least one workflow output using the computing device shown in FIG. 2.

FIG. 3 is a flow diagram 300 of an exemplary method for generating at least one workflow output using a computing device, such as computing device 120 (shown in FIGS. 1 and 2), that includes a user interface and a display interface, such as user interface 150 (shown in FIG. 2) and display interface 136 (shown in FIG. 2). This method may be embodied within a plurality of computer-executable instructions stored in one or more memories, such as one or more computer-readable storage medium 170 (shown in FIG. 2). As described above, computer storage mediums 170 can include non-transitory media and may include volatile and nonvolatile, removable and non-removable mediums implemented in any method or technology for storage of information such as computer-readable instructions, data structures, program modules, such as functionality modules 172 (shown in FIG. 2) or other data. The instructions may be executed by one or more processors, such as processor 130 (shown in FIG. 2), to perform the functions described herein.

In step 302, computing device 120 can receive at least one input from a user, via user interface 136, to generate at least one desktop, such as desktop 140 (shown in FIG. 2). In step 303, computing device 120 generates at least one desktop, such as desktop 140, such that at least one display image 142 associated with desktop 140, such as display image 142 (shown in FIG. 2), can be viewed by the user via display interface 136. In some embodiments, the application can be started by running a file, such as Visual Scripting.exe, that can be found inside, for example, C:\Program Files\VisualScripting\VisualScripting\bin\Release64-directory.

In step 304, the user selects the relevant functionality modules 172 and/or input prompts 300 that he or she desires for the treatment of a particular patient. Computing device 120 receives the selection in step 305. Based on the selection, computing device 120 generates and/or accesses the selected functionality modules 172 or action packs in step 306. Alternatively, if the modules 172 had been previously generated and stored in memory 132 (shown in FIG. 2), then computing device 120 can identify and extract the modules from memory 132. In some embodiments, as described above, functionality modules 172 or action packs are elements of functionality that are configured to receive, as input, a radiation therapy or radiotherapy parameter or object, such as patient information, course information, image, plan, beam, dose, DVH, and return zero or other suitable types of radiation therapy or radiotherapy parameters. In some embodiments, functionality modules 172 are associated with a plurality of performance tasks such that each functionality module 172 corresponds to a different performance task. The performance tasks can include, but are not limited to, calculate DVH, write DVH to a spreadsheet file, view DVH, create plan, create beam, optimize plan, calculate dose, view dose, export dose to a different file type, export DVH as a different file type, and/or upload the DVH as a different file type to another type of document. In some embodiments, as the user selects and places functionality into the workflow, system 100 can make suggestions as to what would be a logical next functionality, as well as warning the user that the one that's just selected doesn't connect with the previous functionality logically or when inserting a functionality into a workflow that's already built, that it is not a logical placement or the workflow would not work, etc. This could also occur when making the connections between the functionalities, such as the user can select all of the functionalities and place them onto the desktop 140, and then can make the connections. In some embodiments, system 100 can make connection suggestions or automatically connect them or show error messages when connecting two or more functionalities would be, for example, problematic.

Figure 4A:
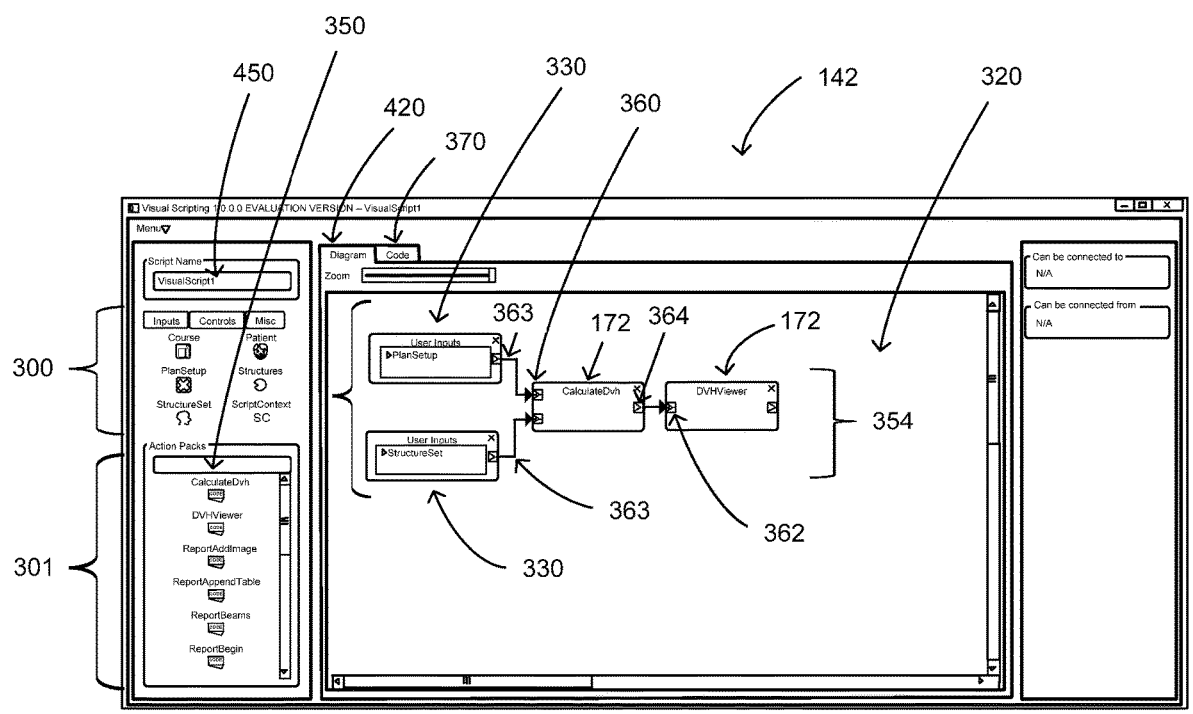
FIGS. 4A-4F are exemplary display images that can be generated by the computing device shown in FIG. 2.

FIG. 4A illustrates an example of one display image 142, wherein the user can see a input components section 300 and a functionality modules section 301 that is associated with functionality modules 172. The user can make various selections from the input components section 300 and functionality modules section 301, via user interface 136.

Referring to FIG. 3, in step 307, the user can select, via user interface 150, various functionality modules 172 that he or she wishes to place on a portion of display image 142. Computing device 120 receives the selection in step 308 and the selected various functionality modules 172 are placed on the pertinent portion of display image 142 in step 309. For example, as shown in FIG. 4A, in some embodiments, the user can, from functionality modules section 301, drag and drop the selected functionality modules 172 onto a canvas portion or middle portion 320 of display image 142.

As shown in FIG. 3, in step 310, using user interface 150, the user can provide an input to connect one of the functionality modules 172 that is placed on middle portion 320 of display image 142 with another functionality module 172 that is placed on middle portion 320 of display image 142. In step 311, computing device 120 receives the input and, in step 312, the connection is made to commence the generation of at least one workflow output. Similarly, in step 313, the user provides an input to connect input components, such as input components 330 (shown in FIG. 4A) to connect to functionality modules 172 that are placed on middle portion 320 of display image 142. In step 314, computing device 120 receives the input and, in step 315, computing device 120 makes the connection to finalize the generation of the workflow output(s).

For example, as shown in FIG. 4A, after identifying an input component 340 from input components section 300, a user can drag and drop input components 340 on middle portion 330 of display image 142. In some embodiments, one input component 340 can have the name "User Inputs" and have an item name, such as "PlanSetup", inside input component 340, while the other input component 340 can also have the name "User Inputs" and have an item name, such as "StructureSet" inside therein. Moreover, as shown in FIG. 4A, in some embodiments, the user can search and identify a pertinent functionality module 172, such as one named "CalculateDvh" using a search prompt 350 in functionality modules section 301, and drag and drop module 172 to middle portion 330 of display image 142. Similarly, the user can search and identify another functionality module 172, such as one named "DVHViewer", and drag and drop the other module 172 to middle portion 330 of display image 142, and on the right side of the other module 172 named "Calculate DvH". Such connections form a diagram 354 on middle portion 330 of display image 142.

In some embodiments, as shown in FIG. 4A, functionality modules 172 can have input ports 360 and output ports 362. In some embodiments, input ports 360 and output ports 362 can be substantially square-shaped, with a triangle-shaped structure 364 inside ports 360 and 362. Alternatively, ports 360 and 362 can have any suitable shape that enables system 100 (shown in FIG. 1) and/or computing device 120 to function as described herein. In some embodiments, input ports 360 are positioned on the left side portion of each module 172 and output ports 362 are positioned on the right side portion of each module 172. A user can create a connection that is, for example, suggested by the system, between input components 340 and modules 172 and also between at least two different modules 172. For example, as shown in FIG. 4A, a connection can be made between the PlanSetup component and the CalculateDvh module by first clicking output port 362 of PlanSetup component and then clicking one of the input ports 360 of the CalculateDvh module. In some embodiments, a connection line 363 appears with an arrow pointing from the PlanSetup component to CalculateDvh module. A connection can be a "suggestion" (i.e., it is not yet in a "ready" state) when it is an arrow with a dash line (not shown). A "ready" connection is an arrow with complete line, such as connection line 363. A user can change the state of the connection from "suggestion" to "ready" by clicking input port 360 where the connection is pointing or by clicking the dashed lines of the connection. All connections must be in the "ready" state when the user is compiling a workflow output or script.

In some embodiments, the user can click output port 362 of, for example, the StructureSet component and then click the free input port 360 (i.e., the one that has no connection arrow pointing to it) of the CalculateDvh module. As such, there can be a valid connection between one input component 340 (i.e., StructureSet component) and one functionality module 172 (i.e., CalculateDvh module). In addition, the user can click output port 362 of the CalculateDvh module and then click input port 360 of the DVHViewer module. As such, there can be a valid connection between two different functionality modules 172.

Figure 4B:
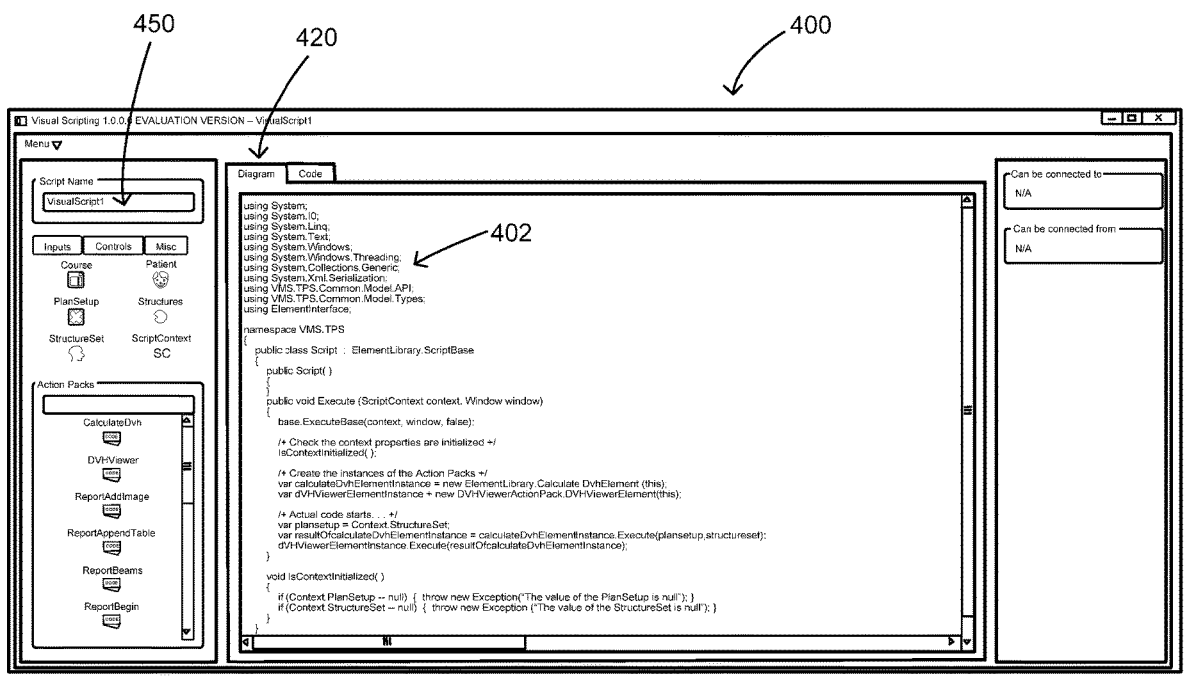

Referring to FIG. 3, when the connections are made, computing device 120 generates at least one code value that is associated with generated workflow output and/or the connections in step 316. In step 317, the user can provide an input to view the code, and computing device 120 receives the input in step 319. In step 320, a different display image is provided by computing device 120 such that the code value(s) can be viewed by the user. Moreover, in step 322, the user can modify or change the code value(s). For example, as shown in FIG. 4A, the user can click on a code tab 370 and computing device 120 provides a different display image 400, as shown in FIG. 4B, wherein display image 400 includes the code values 402, that can be in, for example, C sharp ("C#"). The user can view code values 402 and also directly modify or make any changes to code values 402 using user interface 150. The user can switch back to display image 142 by clicking on a diagram tab 420.

In step 324, referring to FIG. 3, the user can save the generated workflow output and/or save functionality modules 172. In some embodiments, the user can save the workflow output and/or functionality modules 172 directly onto database 160 (shown in FIG. 2) of computing device 120 or, alternatively, the user can save the workflow output and/or functionality modules 172 onto database 160 that is located on, for example, an external server (not shown) such that the file can be shared with remote users. For example, as shown in FIGS. 4A and 4B, the user can rename their script or workflow output to "CalculateAndViewDvh" by changing the name in the "Script Name" section 450, and save diagram 354 and compile it to a plugin by selecting it from a drop down menu, such as Menu->Save and Compile. In some embodiments, a new browser window can open for the user to select a location for the script project or workflow output to be saved and compiled. Inside a folder, for example, the user's selection can create two new directories to store the project files of the diagram and the compiled plugin-scripts. A folder can be selected to save and compile the plugin. A prompt can also be used by computing device 120 to notify the user that the scripts and/or workflow outputs have been successfully saved.

Figure 4C:
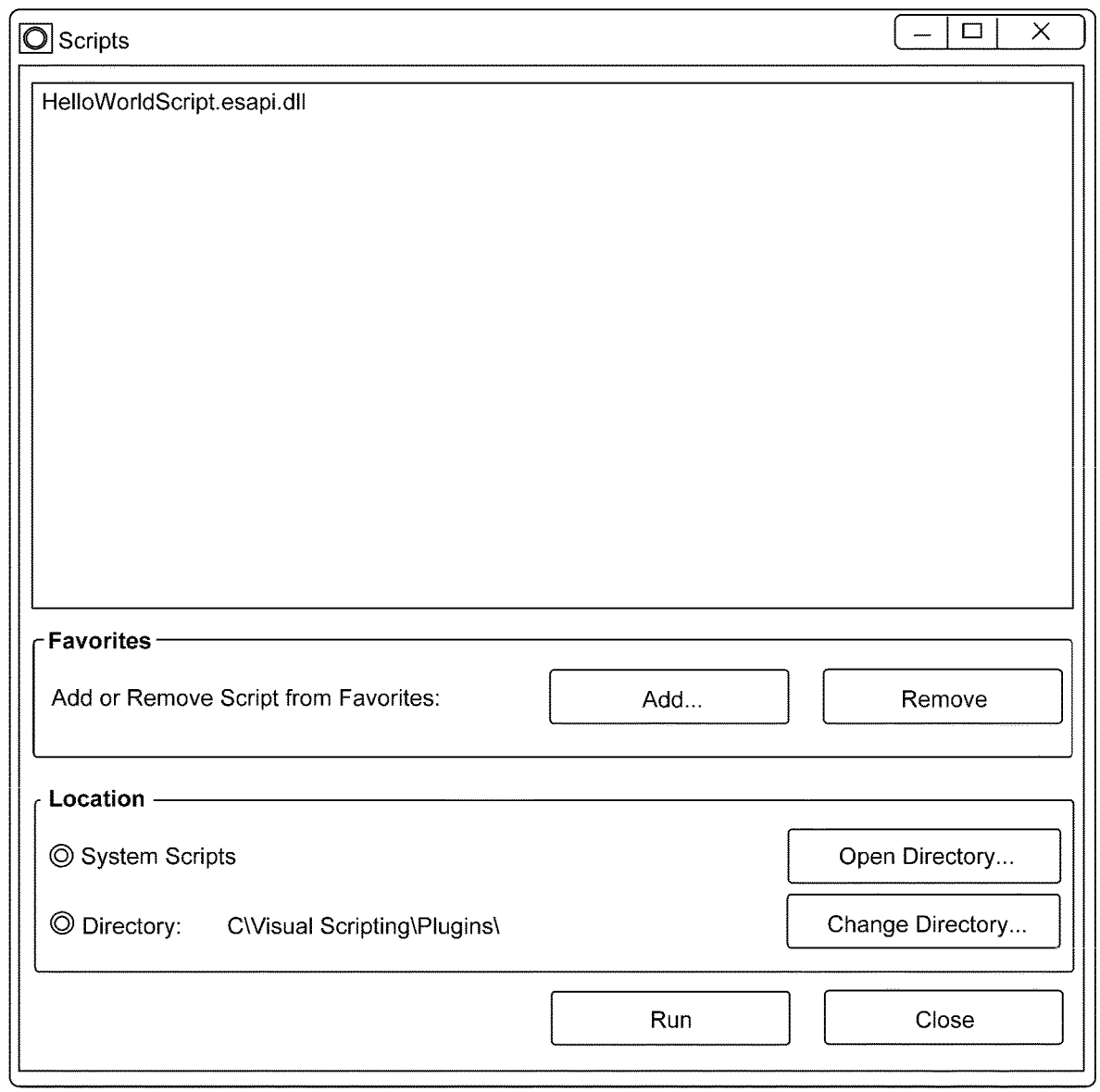
Figure 4D:
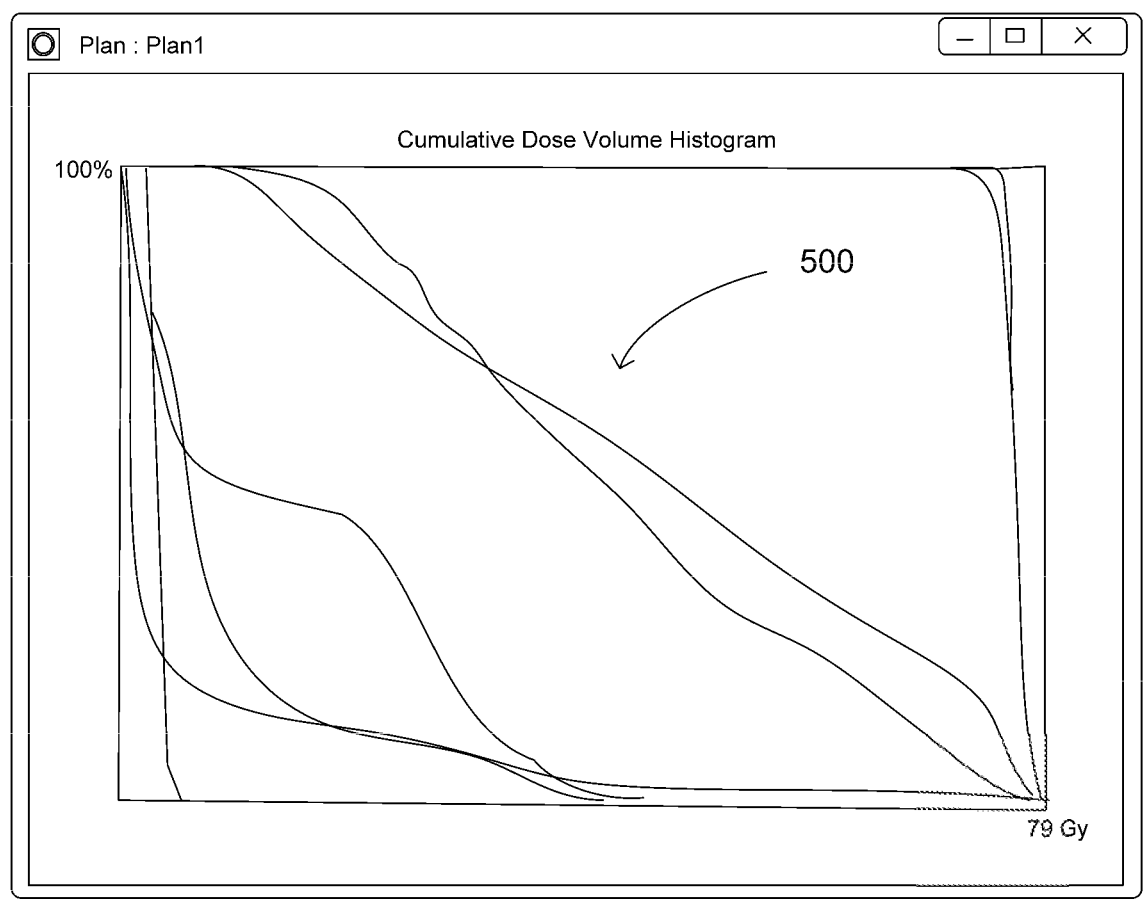

In some embodiments, when performing steps 302-324 above, an integrated development environment (IDE) or a radiotherapy planning system, such as Eclipse, can be used. When using an integrated development environment, the user can run a plugin named "CalculateAndViewDvh.esapi.dll" that is compiled from diagram 354 shown in FIG. 4A. For example, the user can open Eclipse and login with an account number and/or name. The program can use a patient with a "Plan" and "StructureSet". The patient and "Plan" that the user wants to have DVH curves calculated for can be selected, wherein the "Plan" is valid for calculating, for example, DVH curves. The scripts window can be opened by selecting from a menu. The plugin can appear to a script list, such as the "CalculateAndViewDvh.esapi.dll" plugin, as shown in FIG. 4C. The user can select the plugin he or she wants to run and press the "Run" prompt. For example, as shown in FIG. 4D, the "CalculateAndViewDvh" plugin calculates and shows a plurality of DVH curves 500 in a new window or display image 502.

Figure 4E:
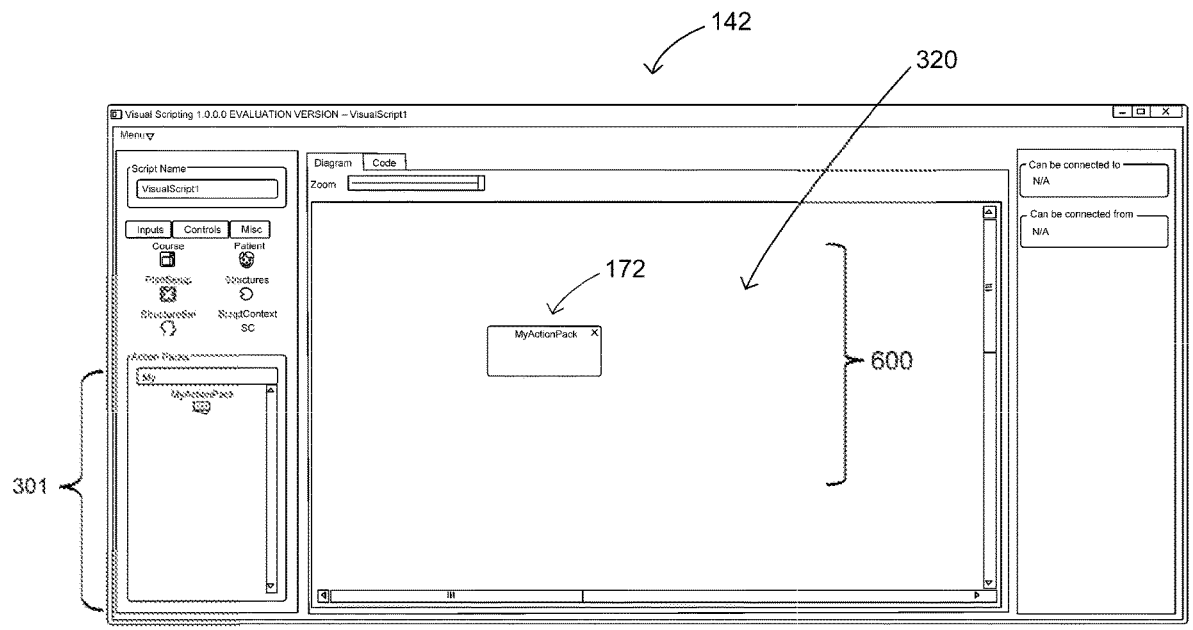
Figure 4F:

In some embodiments, the user can create a custom functionality module 172 or action pack, such as the one named "MyActionPack" shown in FIG. 4E. This creation can be done with, for example, Visual Studio and .NET Framework 4.0. The user can create a new C# Class Library—Project in Visual Studio with .NET Framework 4.0 and give it the name of "MyActionPack". A reference can be made to the ElementInterface.dll assembly in the new project. It can be found inside the Visual Scripting installation directory: C:\Program Files\VisualScripting\VisualScripting\bin\Release64\. The user can change the build configuration platform from any CPU to x64 and rename the generated C# class according to preference and make it derive from the visual scripting element abstract class called "VisualScriptElement". The user can add a constructor without any parameters and a constructor with a parameter, such as IVisualScriptElementRuntimeHost-type. The first one can be at design time (when using an element in, for example, Visual Scripting) and the second one can be when the code is executed in runtime. The user can give a name to module 172 by an override property called "DisplayName". The user can also create a method, such as the one named "MyExecuteMethod" and specify the output type and input parameters. The user can add a C# custom attribute named "ActionPackExecuteMethod" to the "MyExecuteMethod" by adding tag [ActionPackExecuteMethod] before the execute method. In some embodiments, MessageBox can be used so as to add a reference to PresentationFramework. The user can the add a MessageBox to show text "Hello, World!" inside the Execute-method, as shown in FIG. 4F.

An example of a code is shown in Table 1 below.

TABLE 1

Example Code of MyAction Pack.cs-file

```
using ElementInterface;
using System;
using System.Collections.Generic;
using System.Linq;
 using System.Text;
namespace MyActionPack
{
    public class MyActionPack : VisualScriptElement
    {
        public MyActionPack( ) { }
        public MyActionPack(IVisualScriptElementRuntimeHost host) {
        }
        public override string DisplayName
        {
            get { return "MyActionPack"; }
        }
        [ActionPackExecuteMethod]
        public void MyExecuteMethod( )
        {
        System.Windows.MessageBox.Show("Hello, World!");
        }
    }
}
```

The user can compile the project and copy the compiled functionality module 172 shown in FIG. 4E as, for example, "MyActionPack.dll" file, to a folder, such as Visual Scripting ActionPacks folder located in C:\Program Files\VisualScripting\VisualScripting\bin\Release64\. The user can also run system 100 and add the newly created functionality module 142 to a diagram 600 by dragging and dropping it to middle portion 320 of display image 142, as shown in FIG. 4E. The user can find the functionality module in functionality modules section 301 with the name the user defined in in "DisplayName" property. The created functionality module 172 can be on diagram 600 in middle portion 320 of display image 142, as shown in FIG. 4E. The user can compile the diagram and run the script in, for example, Eclipse. The user can then see a new pop-up window showing "Hello, World!", as shown in FIG. 4F. In some embodiments, the user can start by selecting a pre-selected or pre-made pack of functionalities from a plurality of pre-made packs and then make any modifications.

Figure 5:
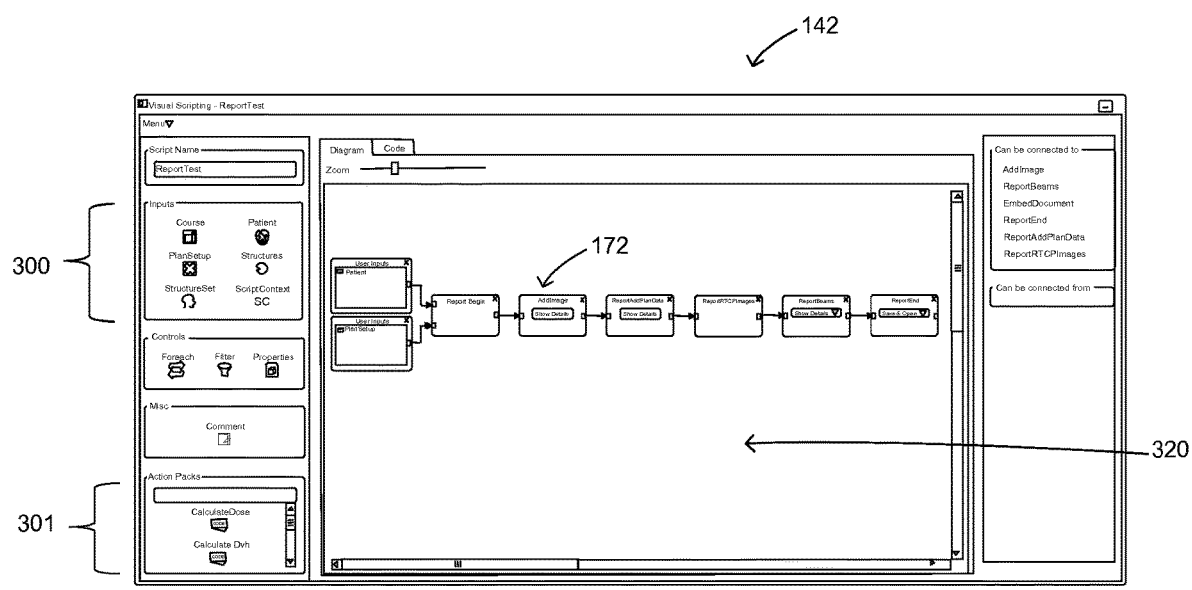
FIG. 5 is an additional exemplary display image that can be generated by the computing device shown in FIG. 2.

In some embodiments, functionality modules 172 can be treatment plan summary generators and when performing steps 302-324 above, a treatment plan report can be generated with the treatment plan summary generators. For example, when performing steps 302-324 above, the user can drag and drop reporting functionality modules 172 or action packs onto middle portion 320 of display image 142 and connect them together. For example, as shown in FIG. 5, a report builder script can start with functionality module 172 named "Report Begin" and end with functionality module 172 named "Report End". Functionality modules 172 can be (a) treatment plan summary generators that provide a plan summary in tabular format, (b) treatment field summary generators that provide field summaries in the report in a tabular format, (c) image generators that provide axial, coronal, sagittal, and arbitrary planar cuts and projection view images into the report, and (d) graph generators to put DVH and other graphs into the reports. Functionality modules 172 can be parameterized such that the user can control page layout and other suitable aspects of the report generation. Moreover, the user can integrate in other functionality modules 172 into the reporting scripts to execute actions needed to generate the report. For example, while reporting plan quality metrics, other visual scripting functionality modules 172 can be used to combine organ pairs (e.g., left and right kidneys to make a total kidney) using scripted structure boolean operators to report metrics on the combined volume of the organ pair. The user can also edit the resulting script code for the generated report to make any modifications by performing steps 316-322 described above.

Exemplary embodiments of systems and methods are described above in detail. The systems and methods are not limited to the specific embodiments described herein, but rather, components of each system and/or method may be utilized independently and separately from other components described herein. For example, each system may also be used in combination with other systems and is not limited to practice with only systems as described herein. Rather, the exemplary embodiment can be implemented and utilized in connection with many other applications.

Although specific features of various embodiments of the invention may be shown in some drawings and not in others, this is for convenience only. In accordance with the principles of the invention, any feature of a drawing may be referenced and/or claimed in combination with any feature of any other drawing.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A system comprising:
   at least one computing device comprising a user interface and a display interface, wherein said at least one computing device is configured to:
   generate at least one desktop that can be viewed by a user via said display interface;

access a plurality of functionality modules that are each configured to receive at least one radiotherapy parameter, each functionality module in the plurality of functionality modules corresponding to software for performing a particular radiotherapy task;

place, via said user interface, the plurality of functionality modules onto the at least one desktop, each functionality module in the plurality being represented on the at least one desktop by a separate graphical user interface (GUI) representation;

connect, via said user interface, one of the placed plurality of functionality modules to at least another one of the placed plurality of functionality modules by linking on the at least one desktop, the GUI representations corresponding to the functionality modules to be connected, thereby commencing the generation of at least one workflow output; connect, via said user interface, a plurality of input components to the placed plurality of functionality modules to update and finalize the generation of the at least one workflow output wherein the system, when functionality modules are connected, makes a suggestion as to what would be a logical next functionality module or indicate a warning for functionality modules that do not logically connect, based on previously connected functionality modules; and generate at least one code value associated with the at least one workflow output wherein the workflow output is used for treating a patient.

2. The system in accordance with claim 1, wherein said at least one computing device is further configured to:
modify, via said user interface, the at least one code value to change the at least one workflow output.

3. The system in accordance with claim 1, wherein said at least one computing device is further configured to save the at least one workflow output.

4. The system in accordance with claim 1, wherein said at least one computing device is further configured to save the plurality of functionality modules.

5. The system in accordance with claim 1, wherein the plurality of functionality modules are associated with a plurality of performance tasks such that each of the plurality of functionality modules corresponds to a different performance task.

6. The system in accordance with claim 1, wherein the plurality of functionality modules are treatment plan summary generators.

7. The system in accordance with claim 6, wherein said at least one computing device is configured to connect, via said user interface, the plurality of functionality modules that are treatment plan summary generators such that a treatment plan report is generated.

8. A method for generating at least one workflow output using a computing device that includes a user interface and a display interface, wherein said method comprises:
generating at least one desktop, via the computing device, that can be viewed by a user via the display interface;
accessing a plurality of functionality modules that are each configured to receive at least one radiotherapy parameter, each functionality module in the plurality of functionality modules corresponding to software for performing a particular radiotherapy task;
placing, via the user interface, the plurality of functionality modules onto the at least one desktop, each functionality module in the plurality being represented on the at least one desktop by a separate graphical user interface (GUI) representation;
connecting, via the user interface, one of the placed plurality of functionality modules to at least another one of the placed plurality of functionality modules by linking on the at least one desktop, the GUI representations corresponding to the functionality modules to be connected, thereby commencing the generation of at least one workflow output; connecting, via the user interface, a plurality of input components to the placed plurality of functionality modules to update and finalize the generation of the at least one workflow output wherein the system, when functionality modules are connected, suggests a logical next functionality module or indicate a warning for functionality modules that do not logically connect, based on previously connected functionality modules; and
generate at least one code value associated with the at least one workflow output wherein the workflow output is used for treating a patient.

9. The method in accordance with claim 8, further comprising:
modifying, via the user interface, the at least one code value to dynamically change the at least one workflow output.

10. The method in accordance with claim 8, further comprising saving the at least one workflow output.

11. The method in accordance with claim 8, further comprising saving the plurality of functionality modules.

12. The method in accordance with claim 8, wherein the plurality of functionality modules are associated with a plurality of performance tasks such that each of the plurality of functionality modules corresponds to a different performance task.

13. The method in accordance with claim 8, wherein the plurality of functionality modules are treatment plan summary generators.

14. The method in accordance with claim 13, further comprising connecting, via the user interface, the plurality of functionality modules that are treatment plan summary generators such that a treatment plan report is generated.

15. At least one non-transitory computer-readable storage medium having computer-executable instructions embodied thereon, wherein, when executed by at least one processor, the computer-executable instructions cause the at least one processor to:
generate at least one desktop that can be viewed by a user via a display interface;
access a plurality of functionality modules that are each configured to receive at least one radiotherapy parameter, each functionality module in the plurality of functional modules corresponding to software for performing a particular radiotherapy task;
place, based on at least one instruction received from the user via the user interface, the plurality of functionality modules onto the at least one desktop each functionality module in the plurality being represented on the at least one desktop by a separate graphical user interface (GUI) representation;
connect, based on at least one instruction received from the user via the user interface, one of the placed plurality of functionality modules to at least another one of the placed plurality of functionality modules by linking on the at least one desktop, the GUI representations corresponding to the functionality modules to be connected, thereby commencing the generation of at least one workflow output;
connect, based on at least one instruction received from the user via the user interface, a plurality of input components to the placed plurality of functionality modules to update and finalize the generation of the at least one workflow output wherein the system, when functionality modules are connected, suggests what would be a logical next functionality module or indicated a warning for functionality modules that do not logically connect, based on previously connected functionality modules; and generate at least one code value associated with the at least one workflow output wherein the workflow output is used for treating a patient.

16. The at least one non-transitory computer-readable storage medium in accordance with claim 15, wherein the computer-executable instructions further cause the at least one processor to:

modify the at least one code value to dynamically change the at least one workflow output, based on at least one instruction received from the user via the user interface.

17. The at least one non-transitory computer-readable storage medium in accordance with claim 15, wherein the computer-executable instructions further cause the at least one processor to save the at least one workflow output.

18. The at least one non-transitory computer-readable storage medium in accordance with claim 15, wherein the computer-executable instructions further cause the at least one processor to save the plurality of functionality modules.

19. The at least one non-transitory computer-readable storage medium in accordance with claim 15, wherein the plurality of functionality modules are treatment plan summary generators.

20. The at least one non-transitory computer-readable storage medium in accordance with claim 19, wherein the computer-executable instructions further cause the at least one processor to connect the plurality of functionality modules that are treatment plan summary generators such that a treatment plan report is generated, based on at least one instruction received from the user via the user interface.

* * * * *